United States Patent [19]
Andera et al.

[11] Patent Number: 5,216,458
[45] Date of Patent: Jun. 1, 1993

[54] APPARATUS AND METHOD FOR TESTING VISUAL ACCUITY AND CONTRAST SENSITIVITY

[75] Inventors: Joseph F. Andera, Palatine; Pete Kaldis, Norridge; Richard J. Unger, Chicago, all of Ill.

[73] Assignee: Stereo Optical Company, Inc., Chicago, Ill.

[21] Appl. No.: 701,491

[22] Filed: May 16, 1991

[51] Int. Cl.$^5$ .................................... A61B 3/02
[52] U.S. Cl. ...................... 351/243; 351/246
[58] Field of Search ............... 351/221, 239, 242, 243, 351/247, 246

[56] References Cited

U.S. PATENT DOCUMENTS

| | | |
|---|---|---|
| 2,280,297 | 4/1942 | Neumueller et al. ............... 351/239 |
| 2,543,179 | 2/1951 | Land et al. . |
| 4,365,873 | 12/1982 | Ginsburg . |
| 4,844,607 | 7/1989 | Andera et al. . |

Primary Examiner—Rodney B. Bovernick
Attorney, Agent, or Firm—Mark I. Feldman

[57] ABSTRACT

A vision testing apparatus and a method for testing vision in terms of contrast sensitivity and spatial frequency response are provided. The apparatus and method utilize a plurality light-polarizing optotypes which are provided on sheets of an oriented polymeric material. The optotypes are presented one at a time to a patient in conjunction with a polarizing filter such that rotation of the filter relative to the optotype will cause the contrast of the optotype to vary from a first condition wherein the pattern of the optotype is indistinguishable from its background to a second condition wherein the optotype is seen at a maximum level of contrast. The patient will indicate the point at which he or she first sees the optotype. The sequential presentation of a series of optotypes having patterns which vary in their spatial frequencies will provide a measure of both contrast sensitivity and spatial frequency response for each patient tested.

20 Claims, 3 Drawing Sheets

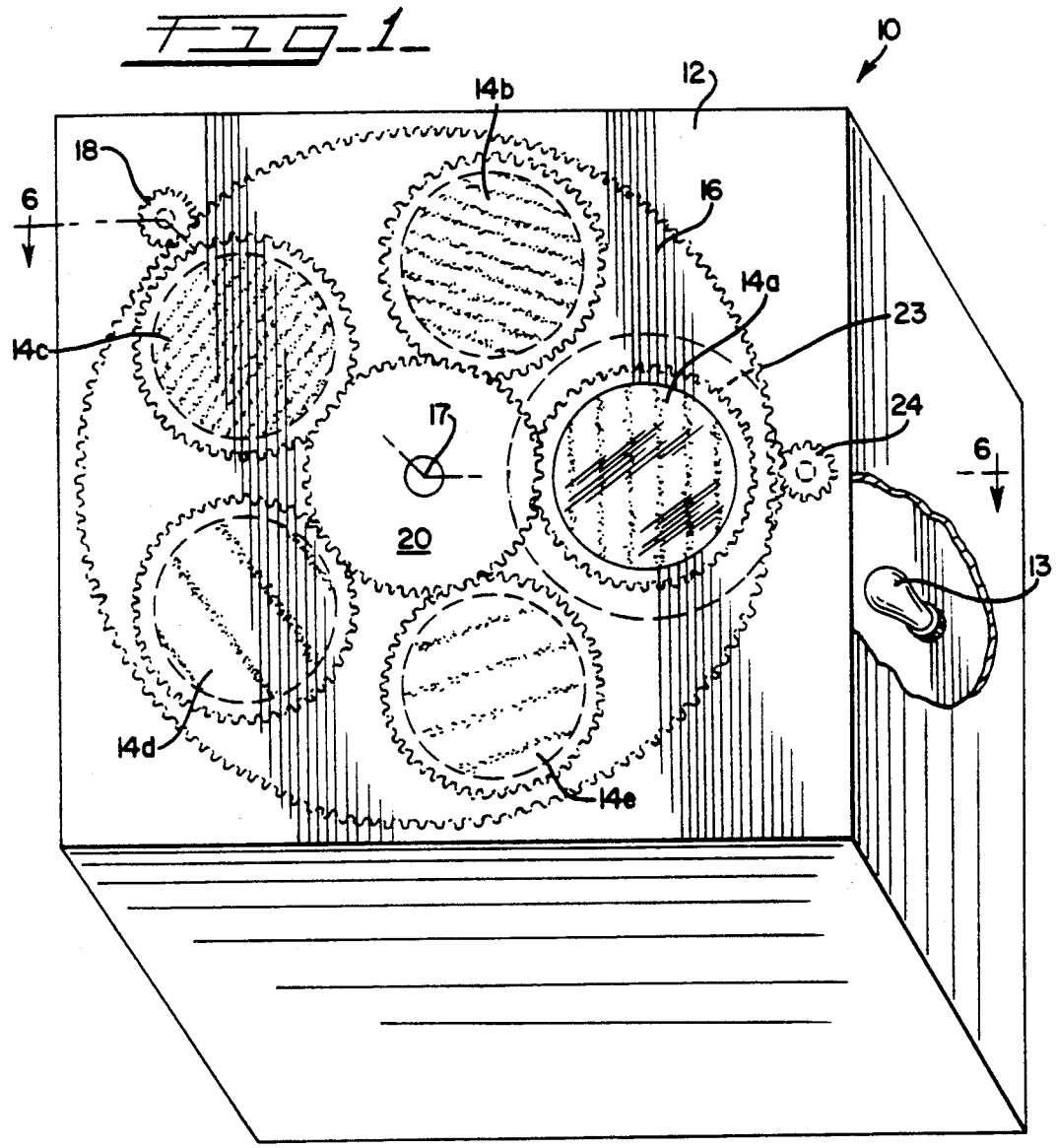

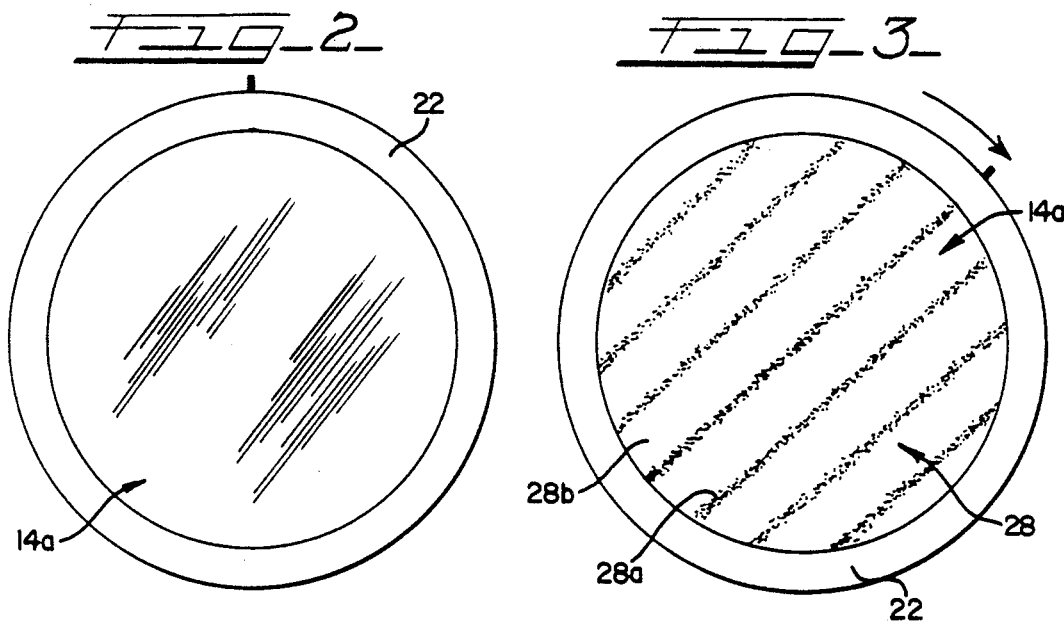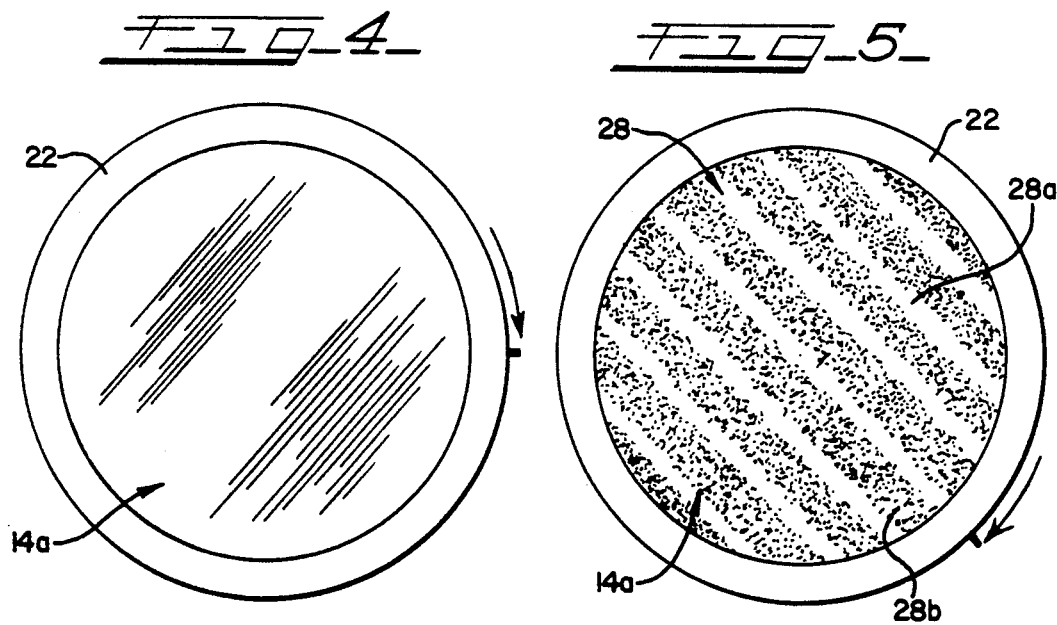

APPARATUS AND METHOD FOR TESTING VISUAL ACCUITY AND CONTRAST SENSITIVITY

BACKGROUND AND BRIEF DESCRIPTION

The present invention relates generally to a vision testing apparatus and a method for testing vision in terms of contrast sensitivity and spatial frequency response. The apparatus includes light-polarizing optotypes which are useful in the testing of vision. The optotypes are viewed through a crossed-analyzer or light-polarizing filter. The light-polarizing characteristics of both the polarizing filter and the optotype is advantageously utilized in a method wherein the rotation of the filter causes the optotype to vary from a first condition, in which a pattern of the optotype is indistinguishable from its background, to a second condition in which the pattern is at a maximum level of contrast. During rotation of the filter, the patient will indicate a point at which he or she first detects the pattern of the optotype to thereby indicate the patient's contrast sensitivity to a particular pattern. The sequential presentation of a series of patterns having different spatial frequencies allows for the evaluation of a patient's spatial frequency response and for the further determination of a functional relationship between contrast sensitivity and spatial frequency response.

Spatial frequency and contrast sensitivity measuring devices are generally known in the art. For example, U.S. Pat. No. 4,365,873 describes a spatial frequency and contrast sensitivity test chart utilizing a multiplicity of grating patches which vary in their levels of relative contrast and also present differing spatial frequencies. The threshold levels of contrast sensitivity and spatial frequency response at which the presence of a grating can be detected accurately is reported to define a visual transfer function.

Such prior art devices and methods for using such devices have generally been limited to the use of charts such as those described in the aforementioned letters patent. The reliance on standard charts requires an extensive collection of gratings or patterns to fully evaluate the patient's so-called transfer function. Such charts generally fail to retain a consistent luminosity across the entire chart and from one grating or pattern to the next. Further, the use of charts presents a bias in the test procedure where the patterns or gratings are presented on a generally white background, such as is provided in the aforementioned Letters Patent. The use of white backgrounds for presenting a series of patterns or gratings is believed to bias the contrast sensitivity measurement in that the patient can view and compare the stark differences in contrast between the white background and the patterns thereon to obtain an additional clue during the determination of contrast sensitivity.

The present invention overcomes the aforementioned shortcomings, by providing an apparatus and a method for using the apparatus which includes means for presenting light-polarizing optotypes which may be viewed through a crossed analyzer or polarizer to determine contrast sensitivity and spatial frequency response for each of a series of such optotypes presented to the patient. By utilizing the light-polarizing qualities of the polarizer and the aforementioned light-polarizing optotype, thresholds of contrast sensitivity may be directly measured on a single optotype merely by rotation of the polarizer relative thereto or by rotation of the optotype relative to the polarizer. By rotation of the polarizer, the pattern of the optotype is slowly brought into higher contrast from an initial point wherein the pattern cannot be visually detected or distinguished from a background. The patient's sensitivity to spatial frequency may be tested by sequentially presenting a plurality of optotypes having different patterns which vary in their spatial frequencies to determine a threshold at which the patient is able to discern the presence of the pattern of that optotype from its background.

In a preferred embodiment, the apparatus of the present invention may be provided with a carousel capable of holding a plurality of optotypes to be presented individually to the patient. A single crossed analyzer or polarizer is provided in association with a light source and the carousel may be driven on command to position the individual optotypes in front of the light source and in association with the polarizer. The optotypes are prepared in a known manner on a transparent or translucent, oriented, linear polymeric material, such as oriented polyvinyl alcohol. The pattern of the optotype used to test spatial frequency response may be any pattern which is substantially uniformly repetitious. A plurality of optotypes having patterns of different spatial frequencies are positioned within the apparatus to facilitate testing.

In use, the apparatus can be used to measure contrast sensitivity by presenting a first optotype to be viewed by the patient through the polarizing filter. The polarizer is initially positioned with respect to the optotype to present the patient with a substantially uniformally transparent or translucent sheet on which no clear pattern is observable. Rotation of the analyzer, relative to the optotype, will gradually bring the pattern into view. While the analyzer is slowly rotated from its aforementioned initial position, the patient will indicate the point at which the pattern of the optotype can first be detected to indicate the patient's contrast sensitivity. An evaluation of spatial frequency response is accomplished by the sequential presentation of several optotypes to cover a range of spatial frequencies. The sequential presentation of a number of optotypes determines the patient's ability to detect or distinguish between the light and dark areas of the patterns, as presented, and thereby provides a measure of the patient's spatial frequency response. A transfer function for the patient is determined by sequentially presenting a number of optotypes to the patient until a low contrast level prevents the patient from detecting the pattern of the optotypes. The patient's threshold levels for contrast level and spatial frequency are quantified and compared with established norms.

It is accordingly an object of the present invention to provide an apparatus for measuring an individual's contrast sensitivity and spatial frequency response.

It is another object of the invention to provide an apparatus for evaluating spatial frequency and contrast sensitivity, the apparatus including means for presenting light-polarizing optotypes to a patient wherein a light polarizing filter is used so that the pattern of the optotype is selectively viewable by rotation of the filter.

It is still another object of the present invention to provide a method for evaluating spatial frequency and contrast sensitivity response which utilizes an apparatus including light-polarizing optotypes in conjunction with a polarizing filter.

BRIEF DESCRIPTION OF THE DRAWINGS

FIG. 1 is a perspective view, in schematic, of an apparatus in accordance with the present invention;

FIG. 2 is a representation, in schematic, of a single optotype and a polarizing filter in accordance with the present invention;

FIG. 3 is a representation of the optotype and polarizing filter of FIG. 2 with the filter rotated 45 degrees;

FIG. 4 is a representation of the optotype and filter of FIG. 2 with the filter rotated 90 degrees;

FIG. 5 is a representation of the optotype and filter of FIG. 2 with the filter rotated 135 degrees.

DETAILED DESCRIPTION OF THE PREFERRED EMBODIMENT

Figure 6:
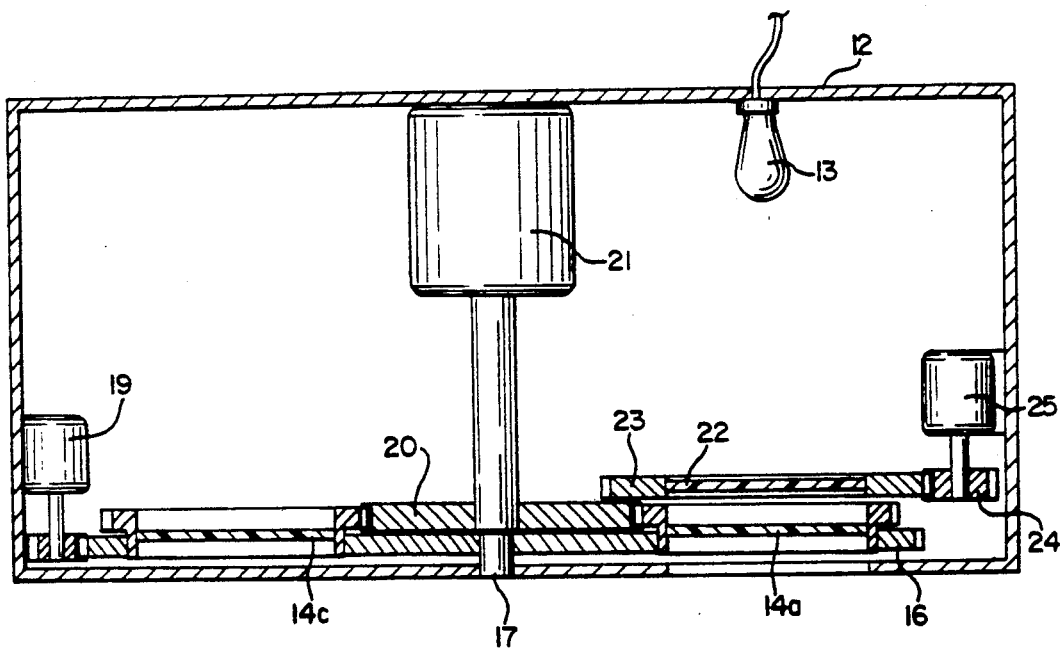
FIG. 6 is a sectional view of the apparatus of FIG. 1, taken along the 6—6 line thereof.

The features of the present invention may best be understood with reference to the following description wherein reference is made to the several figures with like reference numerals indicating like elements.

Referring now to FIG. 1, an apparatus 10 is depicted, in schematic, in accordance with the principles of the present invention. The apparatus is provided with a housing 12 in which a light source 13 is positioned to illuminate a film 14a. The light source 13 is preferably color-corrected in order to achieve translumination of an especially white character. A light source such as that described in U.S. Pat. No. 4,844,607, the subject matter of which is incorporated by reference hereinto, is preferred. As is discussed in the aforementioned Letters Patent, the bulb is of conventional configuration including a tungsten filament enclosed in a clear glass bulb affixed to a screw-type base o other suitable base. The glass bulb has a blue filtering coating applied thereto. The coating is of a thickness to permit filtering or color correcting of the light emitted by the bulb to increase the contrast thereof to obtain a color temperature of approximately 5000°°K. to 5500°°K. and preferably about 5000°°K. to 5200°°K. to maintain substantially consistent illumination of the film 14a through variations in line voltages of between about 110 volts and about 135 volts. It will be understood that "substantially consistent illumination" refers to illumination by the light source 13 which is white in color and which avoids off-color illumination including the development of orange and yellow tinged illumination of film 14a at line voltages between about 110 volts and about 135 volts.

The film is retained on a carousel 16 within a first plane. The carousel 16 will be capable of retaining a plurality of such film components, such as film units 14a-e, and may be rotated about its axis 17 to sequentially position each of the individual film components in front of the light source. The light source will illuminate only one of the film components at a time, such as the film 14a shown in FIG. 1. The carousel 16 can be driven in a manner which is well known to those skilled in the art and, in the device depicted in FIG. 1, the carousel is driven by a drive motor 19 (FIG. 6) within the housing 12 which powers carousel drive gear 18. As shown, the carousel 16 and the carousel drive gear 18 may be provided as a pair of complimentary planetary gears wherein the drive gear 18 can advance the position of the films under the power of drive motor 19 which may be provided as a stepping motor or as a continuous drive motor or other similar device.

The individual films 14a-e may be rotated by a separate drive motor 21 which drives the pattern drive gear 20. In this manner, the optotypes of each of the films can be oriented as desired. This aspect of the invention is further discussed below. The apparatus 10 is also provided with means by which a polarizer 22 can be mounted for use with the film 14a and the light source 13. As shown in FIGS. 1 and 6, the polarizer 22 is mounted on a mounting gear 23 which may be provided in the form of a planetary gear. The polarizer is generally positioned in a second plane which is substantially parallel to the film 14a and is rotatably driven by polarizer drive gear 24 and a motor 25 mounted within housing 12. Again, the drive motor 25 may be a stepping motor or continuous drive motor or the like which provides rotational drive to the gear 24 to rotate mounting gear 23 and the polarizer 22 for selectively altering the contrast of the optotype on the film 14a, as is further discussed below.

It should be appreciated that the apparatus depicted in FIG. 1 is a schematic representation of the preferred embodiment of a device made in accordance with the principles of the present invention. Other such devices are contemplated as within the scope of the invention wherein other means may be employed to position a plurality of film components, such as the films 14a-e, in front of a light source and in association with a polarizer for the testing of spatial frequency and contrast sensitivity. Those skilled in the art will appreciate that even the manual placement of individual light-polarizing optotypes with a polarizing filter in front of a light source is within the scope of the present invention for testing contrast sensitivity and spatial frequency response.

Referring generally to FIGS. 2 through 5, a schematic representation is provided of the film 14a with a polarizer 22 positioned between the light source 13 and the patient or observer. Referring to the film 14a, an optotype 28 which is provided thereon is suitable for the testing of spatial frequency and contrast sensitivity. The optotype used in conjunction with the apparatus 10 herein may have a pattern similar to the pattern or grating utilized in the aforementioned U.S. Pat. No. 4,365,873, for example, the subject matter of which is incorporated by reference hereinto. A plurality of such optotypes will be required to adequately 30 test a patient's vision in accordance with the present invention. Generally, any optotype with a pattern which is substantially uniformly repetitious is suitable.

The film 14a is preferably prepared in accordance with the process described in U.S. Pat. No. 2,543,179, the subject matter of which is incorporated by reference hereinto, to provide a light-polarizing optotype 28 thereon. As mentioned, the optotype 28 on film 14a includes a pattern 28a and a background 28b. Adjustment of the polarizer relative to the optotype, will enhance or decrease the contrast level of the image and the background of the optotype. The optotype will be relatively faint to the naked eye, requiring the use of polarizer 22 which, when oriented in one relative position, 45° with respect to the film 14a, will cause the light-polarizing optotype on the film to appear as sharp as a photographic print with pattern 28a appearing as bold dark areas on a light background 28b. (FIG. 3). Rotation of the polarizer 90° from the first relative position of FIG. 2 to a third relative position will cause the pattern to disappear into the background of the film 14a (FIG. 4) presenting a film which is substantially uniformly transparent or translucent to the patient or observer. Further rotations of polarizer 22 an additional 45° to a fourth relative position (FIG. 5) will provide a negative pattern to appear on film 14a wherein the background 28b now appears as bold dark areas with pattern 28a appearing much lighter than the background. Background 28b and pattern 28a will again appear indistinguishable when the polarizer 22 is positioned at a fifth relative position to complete a full 180° arc of rotation.

In this manner, rotation of the polarizer over an arc of 180° establishes infinitely variable conditions for infinitely variable positions of the polarizer relative to the optotype 28. It will be appreciated that the same effect can be achieved by rotation of the optotype relative to the polarizer and any such relative adjustment of the polarizer or the optotype is within the scope of the present invention. Preferably, contrast levels between background 28b and pattern 28a used herein will generally range from 30% when the image is observable at a maximum contrast level to zero when the pattern is indistinguishable from its background, defining contrast in terms of maximum and minimum luminance levels:

$$C = \frac{(L_1 - L_2)}{(L_1 + L_2)}$$

where $L_1$=maximum luminance and $L_2$=minimum luminance. Calibration of the contrast levels provided by the position of the polarizing filters relative to the optotype can be accomplished in a known manner.

In the method of the present invention, the film 14a is initially positioned so that the pattern 28a is initially oriented in a predetermined manner known only to the operator of the apparatus 10—i.e., so that the pattern is canted to the right, to the left, or straight up and down. Once the pattern 28a on film 14a is oriented in a desired manner, the polarizer 22 is rotated to present the optotype to the patient without an observable pattern, substantially as shown in FIG. 2, for example. The operator of the apparatus 10 can slowly rotate polarizer 22 until the patient indicates to the operator the point at which the pattern 28a first becomes visible. The patient's initial detection of the pattern can be verified by having the patient further indicate the pattern's orientation. The patient's verified response can then be used as a measurement of contrast sensitivity by noting the relative position of the polarizer to indicate the pre-determined contrast level which corresponds thereto.

Spatial frequency response can be tested by sequentially showing the patient optotypes with patterns of varying spatial frequency until the patient indicates an inability to distinguish between the pattern and background areas of a particular optotype. A complete evaluation of spatial frequency response and contrast sensitivity involves the use of a plurality of optotypes to determine the points at which low contrast prevents the patient from detecting the pattern and its orientation. In this manner, the patient's detection thresholds can be quantified and compared with established norms and/or the results of previous examinations.

In the preferred embodiment, the use of light polarizing optotypes has several advantages which are worth noting. The nature of the light polarizing patterns 28a on the background 28b is such that rotation of the polarizing filter 22 will cause the pattern to essentially appear and to disappear in the manner described above. However, the overall luminosity across the film 14a remains constant during the rotation of the filter 22 even though the contrast level between the pattern 28a and the background 28b is changing. In this manner, errors in testing which may result from changes in luminosity are avoided. Such errors are introduced in the testing process by the use of charts, for example, where different patterns may exhibit differing levels of luminosities across a chart because of variations in the uniformity or overall quality of the printing across the chart as well as the use of uneven or inadequate lighting. In the present invention, a single light source provides consistent luminosity across the optotype while the film 14a and polarizer 22 coact so that the pattern 28a and background 28b are varied in their respective intensities to maintain a constant luminosity across the film 14a.

Additionally, use of a light source 13 to illuminate a single film 14a in the manner described herein, eliminates the use of the white background and the inherent problems associated with such backgrounds, as noted above with regard to the type of chart used in U.S. Pat. No. 4,365,873. In the preferred embodiment herein, light source 13 illuminates only the film 14a so that a patient is not able to Compare the differences in contrast between the pattern and a white background, for example, to obtain additional clues regarding either the orientation or the spatial frequency of the pattern. Accordingly, the present invention eliminates an inherent bias of prior art devices by eliminating the use of a white background for the optotype 28.

Although a particular preferred embodiment has been discussed and described herein, it is contemplated that variations of the apparatus depicted herein can be made by those skilled in the art. For example, any apparatus that presents a polarizing optotype in conjunction with a polarizing filter is contemplated as within the scope of the present invention as used for the determination of spatial frequency response and contrast sensitivity. It is further contemplated that the use of such polarizing optotypes and analyzers can be accomplished in conjunction with vision testers presently on the market for the general testing of visual acuity, for example. Such variations to the apparatus and method described herein can be accomplished in the absence of the housing 12, for example. It is further contemplated that an apparatus which embodies the present invention could be made without the use of a carousel. Generally, any means by which a light-polarizing optotype can be presented to an observer by use of a light polarizing filter in the manner discussed herein, is contemplated as being within the scope of this invention.

Accordingly, it will be appreciated that variations and modifications to the preferred embodiment discussed and described herein can be accomplished by those skilled in the art without departing from the true spirit and scope of the present invention.

We claim:

1. An apparatus for testing vision monocularly, comprising:
   a light-polarizing optotype provided on first sheet of material;
   means for presenting said optotype on said first sheet to an abserver, said means including a light source and a polarizing filter, said polarizing filter provided as a second sheet of a material positioned substantially parallel to said first sheet;
   said first sheet and said second sheet being rotatably adjustable between at least a first relative position and a second relative position about an axis, said axis being substantially perpendicular to said first sheet and said second sheet;

whereby, said first sheet appears substantially uniformly transparent to the observer when said first and second sheets are in said first relative position and wherein said optotype on the first sheet is observable to the observer when said first and second sheets are in said second relative position; and said optotype on said first sheet including a pattern and a background such that the observable contrast level between said pattern and said background varies by adjustment of said polarizing filter relative to said optotype about said axis to provide five contrast conditions, including:

a first condition when said polarizing filter is in said first relative position wherein said background and said pattern are indistinguishable to an observer;

a second condition when said polarizing filter is in said second relative position, wherein said pattern is darker than said background;

a third condition when said polarizing filter is in a third relative position wherein said pattern and said background are indistinguishable;

a fourth condition when said polarizing filter is in a fourth relative position wherein said background is darker than said pattern; and a fifth condition when said polarizing filter is in a fifth relative position wherein said pattern and said background are indistinguishable.

2. The apparatus of claim 1 wherein said first sheet is an oriented polymer material.

3. The apparatus of claim 1 wherein said optotype includes a pattern and a background, said optotype providing a constant luminosity thereacross when said polarizing filter is in either said first position or in said second position.

4. The apparatus of claim 1 wherein said image on said first sheet has a perceivable orientation such that said orientation of said optotype on said first sheet is observable by an observer when said polarizing filter is in said second position.

5. The apparatus of claim 1 further comprising:
a housing, said housing containing said light source and having an opening therethrough;
means for mounting said first sheet over said opening for illuminating said optotype with said light source; and
means for retaining said polarizing filter over said opening and in association with said first sheet.

6. The apparatus of claim 5 wherein said means for mounting said first sheet is provided as a carousel rotatably affixed to said housing, said carousel having a plurality of retaining slots, each of said retaining slots being capable of holdign a first sheet therein such that said carousel may be rotated to sequentially align each of said retaining slots around said opening in said housing.

7. The apparatus of claim 1 wherein said light source is an incandescent bulb having blue filtering means positioned on a light transmitting surface thereof, said blue filtering means including a coating having a coloration shade, a thickness and a density that, in cooperation with said light source, provides illumination of said optotype in a range of between about 5,000° K. and about 5,500° K. and maintaining substantially consistent illumination of said optotype through variations in line voltage input to said apparatus of between about 110 and about 135 volts, said substantially consistent illumination being white in color.

8. An apparatus for testing vision, comprising:
a housing containing a light-source, said housing having an opening therethrough;
a light-polarizing optotype provided on a first sheet of a material;
means for mounting said first sheet over said opening for illuminating said optotype with said light source;
a polarizing filter provided as a second sheet of a material positioned substantially parallel to said first sheet and over said second opening; and
said first sheet and said second sheet being rotatably adjustable between at least a first relative position and a second relative position about an axis, said axis being substantially perpendicular to said first sheet and said second sheet;

whereby said first sheet appears substantially uniformly transparent to an observer when said first and second sheets are in said first relative position and wherein said optotype on the first sheet is observable to the observer when said first and second sheets are in said second relative position; and said optotype on said first sheet including a pattern and a background such that the observable contrast level between said pattern and said background varies by adjustment of said polarizing filter relative to said optotype about said axis to provide five contrast conditions, comprising:

a first condition when said polarizing filter is in said first relative position wherein said background and said pattern are indistinguishable to an observer;

a second condition when said polarizing filter is in said second relative position, wherein said pattern is darker than said background;

a third condition when said polarizing filter is in a third relative position wherein said pattern and said background are indistinguishable;

a fourther condition when said polarizing filter is in a fourth relative position wherein said background is darker than said pattern; and a fifth condition when said polarizing filter is in a fifth relative position wherein said pattern and said background are indistinguishable.

9. The apparatus of claim 8 wherein said first sheet is an oriented polymer material.

10. The apparatus of claim 8 wherein said optotype includes a pattern and a background, said optotype providing a constant luminosity thereacross when said polarizing filter is in either said first position or in said second position.

11. The apparatus of claim 8 wherein said optotype on said first sheet has a perceivable orientation such that said orientation of said optotype on said first sheet is observable by an observer when said polarizing filter is in said second position.

12. The apparatus of claim 8 wherein said means for mounting said first sheet over said opening is provided as a carousel rotatably affixed to said housing, said carousel having a plurality of retaining slots, each of said retaining slots being capable of holding a first sheet therein such that said carousel may be rotated to sequentially align each of said retaining slots around said opening in said housing.

13. The apparatus of claim 8 wherein said light source is an incandescent bulb having blue filtering means positioned on a light transmitting surface thereof, said blue filtering means including a coating having a coloration shade, a thickness and a density that, in cooperation with said light source, provides illumination of said optotype in a range of between about 5,000°°K. and about 5,500°°K. and maintaining substantially consistent illumination of said optotype through variations in line voltage input to said apparatus of between about 110 and about 135 volts, said substantially consistent illumination being white in color.

14. A method for testing vision, comprising:
providing a light-polarizing optotype in a first plane;
illuminating said optotype;
providing a light-polarizing filter in a second plane, said first plane and said second plane being substantially parallel to each other and said polarizing filter and said optotype being rotatably adjustable about an axis;
adjusting said polarizing filter relative to said optotype about said axis to a first relative position so that said optotype is not observable to a patient;
presenting said optotype to said patient with said polarizing filter and said optotype in said first relative position;
rotatably adjusting said filter and said optotype relative to eaoh other about said axis through at least 5 positiosn of various contrast conditions; and
reording a patient's response to the position of said filter relative to said optotype at which said patient first observes said optotype.

15. The method of claim 14 wherein said providing of said light-polarizing optotype is accomplished by providing said optotype on a sheet of an oriented polymer material.

16. The method of claim 14 wherein said providing of said light-polarizing optotype is accomplished by mounting a first sheet of polymeric material in a carousel, said first sheet including said light-polarizing optotype thereon, and wherein said illuminating of said optotype is accomplished with a light source positioned within a housing, said housing having an opening therethrough for illuminating said light-polarizing optotype, said carousel having a plurality of retaining slots, each of said retaining slots being capable of holding a first sheet therein, such that said carousel may be rotated to sequentially position each of said retaining slots over said opening in said housing to sequentially present a series of said optotypes to said patient.

17. The method of claim 16 wherein said providing of said light-polarizing filter in said second plane is accomplished by positioning said light-polarizing filter over said opening in said housing such that said polarizing filter is rotatable within said second plane while positioned over said opening.

18. The method of claim 14 wherein said providing of said light-polarizing optotype is accomplished by orienting said optotype within said first plane such that said patient's response can be verified by having said patient indicate the orientation of said optotype.

19. An apparatus for testing vision, comprising:
a light-polarizing optotype provided on a first sheet of material;
means for presenting said optotype on said first sheet to an observer, said means including a light source and a polarizing filter, said polarizing filter provided as a second sheet of a material positioned substantially parallel to said first sheet;
a housing, said housing containing said light source and having an opening therethrough;
means for mounting said first sheet over said opening for illuminating said optotype with said light source;
means for retaining said polarizing filter over said opening and in association with said first sheet;
said first sheet and said second sheet being rotatably adjustable between at least a first relative position and a second relative position about an axis, said axis being substantially perpendicular to said first sheet and said second sheet; and
said means for mounting said first sheet comprising a carousel rotatably affixed to said housing, said carousel having a plurality of retaining slots, each of said retaining slots being capable of holding said first sheet therein such that said carousel may be rotated to sequentially align each of said retaining slots around said opening in said housing;
whereby, said first sheet appears substantially uniformly transparent to the observer when said first and second sheets are in said first relative position and wherein said optotype on the first sheet is observable to the observer when said first and second sheets are in said second relative position.

20. An apparatus for testing vision, comprising:
a housing containing a light-souce, said housing having an opening therethrough;
a light-polarizing optotype provided on a first sheet of a material;
means for mounting said first sheet over said opening for illuminating said optotype with said light source;
a polarizing filter provided as a second sheet of a material positioned substantially parallel to said first sheet and over said opening;
said first sheet and said second sheet being rotatably adjustable between at least a first relative position and a second relative position about an axis, said axis being substantially perpendicular to said first sheet and said second sheet; and
said means for mounting said first sheet over said opening comprising a carousel rotatably affixed to said housing, said carousel having a plurality of retaining slots, each of said retaining slots being capable of holding a first sheet therein such that said carousel may be rotated to sequentially align each of said retaining slots around said opening in said housing;
whereby said first sheet appears substantially uniformly transparent to an observer when said first and second sheets are in said first relative position and wherein said optotype on the first sheet is observable to the observer when said first and second sheets are in said second relative position.

* * * * *